(12) United States Patent
Prucher et al.

(10) Patent No.: US 6,413,989 B1
(45) Date of Patent: Jul. 2, 2002

(54) PIPERIDINYLMETHYLOXAZOLIDINONE DERIVATIVE

(75) Inventors: Helmut Prucher; Gerd Bartoszyk; Christoph Seyfried; Rudolf Gottschlich; Joachim Leibrock, all of Darmstadt (DE)

(73) Assignee: Merck Patent Gesellschaft mit beschrankter Haftung, Darmstadt (DE)

( * ) Notice: Subject to any disclaimer, the term of this patent is extended or adjusted under 35 U.S.C. 154(b) by 0 days.

(21) Appl. No.: 09/508,059

(22) PCT Filed: Aug. 26, 1998

(86) PCT No.: PCT/EP98/05402

§ 371 (c)(1),
(2), (4) Date: May 17, 2000

(87) PCT Pub. No.: WO99/12924

PCT Pub. Date: Mar. 18, 1999

(30) Foreign Application Priority Data

Sep. 9, 1997 (DE) .......................... 197 39 332

(51) Int. Cl.⁷ ....................... A61K 31/45; C07D 413/06
(52) U.S. Cl. ........................ 514/326; 546/209
(58) Field of Search ............................ 546/209; 514/326

(56) References Cited

U.S. PATENT DOCUMENTS 4,970,217 A * 11/1990 Prucher et al. ............. 514/327
5,714,502 A * 2/1998 Prucher et al. ............. 514/326

* cited by examiner

*Primary Examiner*—Patricia L. Morris
(74) *Attorney, Agent, or Firm*—Millen, White, Zelano & Branigan, P.C.

(57) ABSTRACT

The invention relates to the compound 5-[4-(4-fluorobenzyl) piperidin-1-ylmethyl]-3-(4-hydroxy-phenyl)oxazolidin-2-one of the formula I and to physiologically acceptable salts thereof. The compound acts as a neuroleptic.

22 Claims, No Drawings

PIPERIDINYLMETHYLOXAZOLIDINONE DERIVATIVE

The invention relates to the compound 5-[4-(4-fluorobenzyl)piperidin-1-ylmethyl]-3-(4-hydroxy-phenyl)oxazolidin-2-one of the formula I

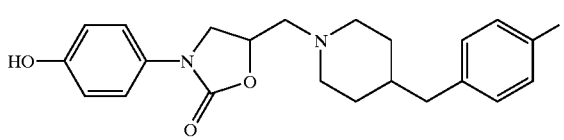

and to physiologically acceptable salts thereof.

The invention relates to the compound of the formula I according to claim 1 and also to its enantiomers and to its salts.

Piperidinylmethyloxazolidone derivatives are known as psychopharmacologically effective substances from EP 0 763 535.

With regard to this protective right, the compound according to the invention should be regarded as a selection invention.

The invention had the object of providing novel compounds which can be employed for the production of medicaments, but which have a more pronounced activity spectrum than the active compounds of the prior art and which act selectively on the central nervous system, have few side effects, can, at the same time, owing to a modified structure, be administered in a dose which is as low as possible and have a very low, if any, addictive potential.

It has now been found that, while being well tolerated, the compound of the formula I and its physiologically acceptable salts have useful pharmacological properties. It displays effects in particular on the central nervous system, and has neuroleptic, tranquillizing, anxiolytic, antidepressive and memory-enhancing actions.

The invention therefore relates to the compound of the given formula I and to salts thereof, and to their use as pharmacologically active compound.

However, the invention also relates to suitable processes for preparing these compounds and/or salts thereof.

Specifically, the compound of the given formula I and salts thereof have neuroleptic action; it inhibits the apomorphine-induced climbing behaviour in mice, the apomorphine-induced stereotypical behaviour in rats (for method see Costall et al., European J. Pharmacol. 50 (1978), 39–50, and Puech et al., European J. Pharmacol. 50 (1978) 291–300, respectively) and the conditioned avoiding reaction in rats (for method see Niemegeers et al., Psychopharmacology 16 (1969), 161–174), without the occurrence of catalepsy (for method see Stanley and Glick, Neuropharmacology 15 (1976), 393–394), which is seen as an indication of the lack of a side-effect potential with respect to extrapyrimidal motor side effects (Hoffmann and Donovan, Psychopharmacology 120 (1995), 128–133). It inhibits ultrasound vocalization after electric stimulation in rats (proof of the anxiolytic action; for method see De Vry et al., European J. Pharmacol. 249 (1993), 331–339) and has a marked effect on the spontaneous behaviour of mice and rats (for method see Irwin, Psychopharmacology 13 (1968), 222–257). Additionally, in the binding experiment this active compound displaces tritiated ifenprodil in the forebrain of rats from its binding site (for method see Schoemaker et al., European J. Pharmacol. 176 (1990), 249–250), which represents a receptor at the N-methyl-D-aspartate (NMDA) receptor/ion channel complex as a subtype of the glutamate receptors.

Based on the glutamate deficiency hypothesis of schizophrenia (Ishimaru and Toru, CNS Drugs 7 (1997), 47–67; Carlsson et al., Int. Acad. Biomed. Drug Res., 4 (1993), 118), substances which display agonistic action at glutamate receptors represent an entirely novel principle of action for the treatment of schizophrenia, whereas customary neuroleptics, in contrast, act directly as antagonists at the dopamine receptor (in accordance with the classic dopamine overactivity hypothesis of schizophrenia, Carlsson et al., Life Sciences 61 (1997), 75'94), with the disadvantage that they cause the typical extrapyrimidal motor side effects which, in some cases, are irreversible after long-term treatment, and which induce mental impairments such as anxiety (Casey, Int. Clinical Psychopharmacology 10 Suppl. 3 (1995), 105–114).

Surprisingly, it has now been found that the 5S-enantiomer of the compound according to the invention is a potent ligand in vitro in the nanomolar concentration range for the polyamine binding site and has, in comparison to the compounds of the formula A, B and C (C see EP 0 763 535; page 9, line 18), neuroleptic actions.

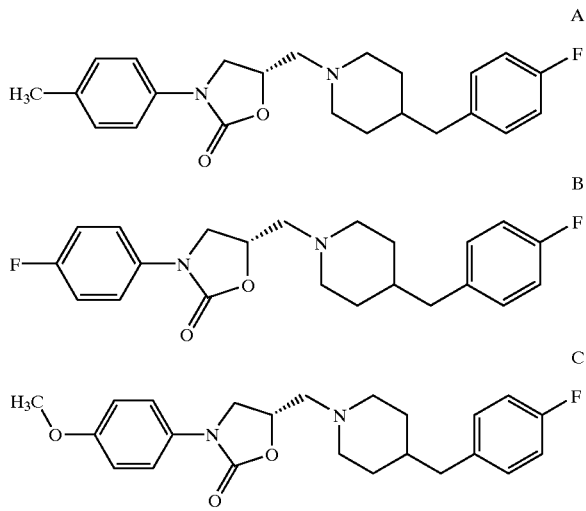

The pharmacological test data are summarized in Table I.

Based on these results of the investigations, it has been found that the compound of the formula I and physiologically acceptable acid addition salts thereof can be used as active compound for medicaments, and also as intermediate for the preparation of other active compounds for medicaments.

The invention furthermore relates to a process for preparing the compound of the formula I according to claim 1, characterized in that a) a compound of the formula II

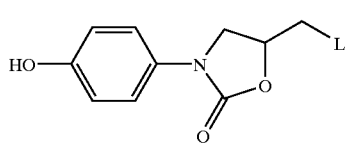

in which

L is Cl, Br, I or a free or reactively functionally modified OH group is reacted with a compound of the formula III

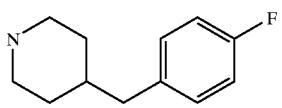

III or
b) a compound of the formula IV

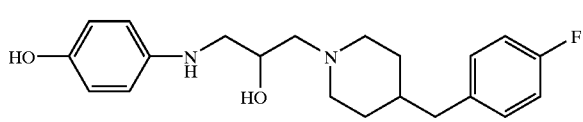

IV is the reacted with a compound of the formula V

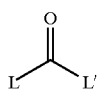

V in which L and L' independently of one another are in each case Cl, Br, I or a free or reactively functionally modified OH group or
c) a compound of the formula VI

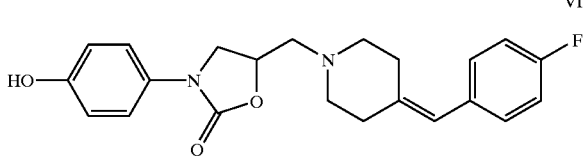

VI is hydrogenated or
d) the compound of the formula I is liberated from one of its functional derivatives by treatment with a solvolysing or hydrogenolysing agent and/or in that a basic compound of the formula I is converted into one of its salts by treatment with an acid.

Otherwise, the preparation of the compounds of the formula I is carried out by methods known per se, as described in the literature (for example in the standard works such as Houben-Weyl, Methoden der Organischen Chemie [Methods of Organic Chemistry], Georg-Thieme-Verlag; J. March, Advanced Organic Chemistry 3rd. Ed. (1984) or Organic Reactions, both John Wiley & Sons, Inc. New York), specifically under reaction conditions known and suitable for the said reactions. It is moreover possible to make use of variants which are known per se but not mentioned here in detail.

The compound of the formula I can preferably be obtained by reacting a compound of the formula II with the compound of the formula III.

Some of the starting materials of the formulae II and III are known. Those which are not known can be prepared by methods known per se.

Primary alcohols of the formulae II are obtainable, for example, by reduction of the corresponding carboxylic acids or esters thereof. Treatment with thionyl chloride, hydrogen bromide, phosphorus tribromide or similar halogen compounds generates the corresponding halides of the formula II.

The compound of the formula III can be prepared, for example, analogously to scheme 1.

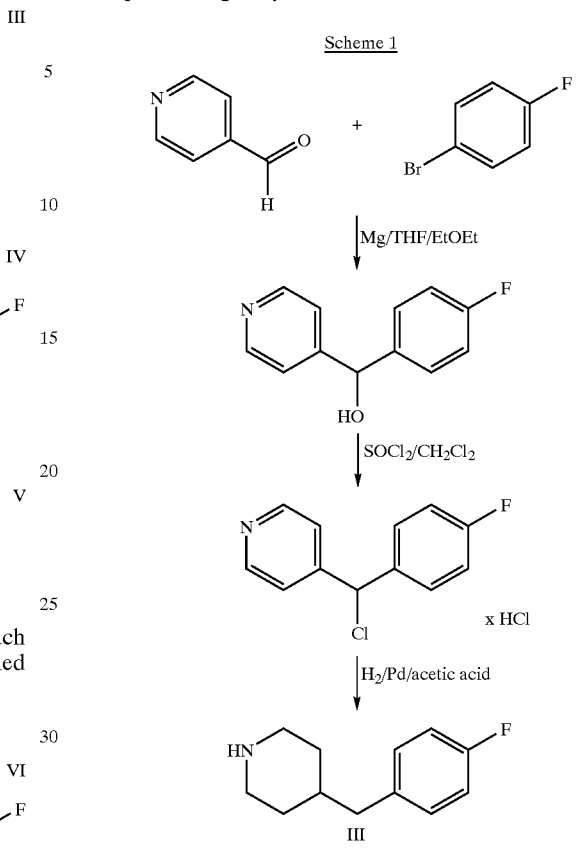

Scheme 1

The reaction of the compounds of the formula II with the compound of the formula III is generally carried out in an inert solvent, in the presence of an acid binder, preferably an alkali metal or alkaline earth metal hydroxide, carbonate or bicarbonate, or another salt of a weak acid of the alkali metals or alkaline earth metals, preferably of potassium, sodium, calcium or caesium. The addition of an organic base, such as triethylamine, dimethylaniline, pyridine or quinoline, may also be favourable. Depending on the conditions employed, the reaction time is between some minutes and 14 days, the reaction temperature is between about 0° and 150°, normally between 20° and 130°.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl ether or ethylene glycol monoethyl ether (methyl glycol or ethyl glycol), ethylene glycol dimethyl ether (diglyme) ; ketones, such as acetone or butanone; amides, such as acetamide, dimethylacetamide or dimethylformamide (DMF); nitriles, such as acetonitrile, sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the abovementioned solvents.

The sulfonyloxy compounds of the formula II can be obtained from the corresponding alcohols by reaction with the appropriate sulfonyl chlorides. The iodine compounds of the formula II can be obtained, for example, by action of potassium iodide on the related p-toluenesulfonyl esters.

Compounds of the formula I can furthermore preferably be obtained by reaction of compounds of the formula IV with compounds of the formula V. Preferred compounds of the formula V are dialkyl carbonates, such as dimethyl, ditrichloromethyl or diethyl carbonate, chloroformates, such as methyl chloroformate or ethyl chloroformate, N,N'-carbonyldiimidazole or phosgene.

Some of the starting materials of the formulae IV and V are known. Those which are not known can be prepared by methods known per se. The reaction is carried out in solvents and at temperatures as described above.

The compound of the formula VI can furthermore be converted reductively into the compounds of the formula I. To this end, preference is given to using catalytic hydrogenation with, for example, palladium on activated carbon and hydrogen.

Furthermore, it is possible to obtain a compound of the formula I by treating a precursor, which contains one or more reducible group(s) and/or one or more additional C—C and/or C–N bond(s) instead of hydrogen atoms, with a reducing agent, preferably at temperatures between −80 and 250° C. in the presence of at least one inert solvent.

Reducible groups (groups which can be replaced by hydrogen) are, in particular, oxygen in a carbonyl group, hydroxyl, arylsulfonyloxy (for example toluene sulfonyloxy), N-benzenesulfonyl, N-benzyl or O-benzyl.

In principle, it is possible to reductively convert compounds which contain only one or those which contain jointly two or more of these groups or additional bonds into a compound of the formula I. To this end, preference is given to using catalytic hydrogenation of nascent hydrogen or certain complex metal hydrides, such as $NaBH_4$ or $LiAlH_4$.

Suitable for use as catalysts for the catalytic hydrogenation are, for example, noble metal, nickel and cobalt catalysts. The noble metal catalysts may be present on supports (for example platinum or palladium on carbon, palladium on calcium carbonate or strontium carbonate), oxide catalysts (for example platinum oxide), or as finely divided metal catalysts. Nickel and cobalt catalysts are advantageously employed as Raney metals, and nickel also on diatomaceous earth or pumice as support. The hydrogenation can be carried out at room temperature and at atmospheric pressure, or else at elevated temperature and/or elevated pressure.

Preference is given to carrying out the reaction at pressures between 1 and 100 bar and at temperatures between −80 and +150° C., primarily between room temperature and 100° C. The reaction is advantageously carried out in the acidic, neutral or basic range and the presence of a solvent, such as water, methanol, ethanol, isopropanol, n-butanol, ethyl acetate, dioxane, acetic acid or THF, it being additionally possible to employ mixtures of these solvents.

If the reducing agent used is nascent hydrogen, his can be generated, for example, by treating metals with weak acids or with bases. Thus, it is possible to employ, for example, a mixture of zinc and aqueous alkali metal solution or iron and acetic acid. It is also suitable to employ sodium or another alkali metal in an alcohol such as ethanol, isopropanol, butanol, amyl alcohol or isoamyl alcohol or phenol. Furthermore, it is possible to use an aluminium/nickel alloy in alkaline-aqueous solution, if appropriate with addition of ethanol. Sodium amalgam or aluminium amalgam in aqueous-alcoholic or aqueous solution are also suitable for generating the nascent hydrogen. The reaction can also be carried out in heterogeneous phase, in which case an aqueous and a benzene or toluene phase are advantageously employed.

Suitable reducing agents are furthermore complex metal hydrides, such as $NaBH_4$, diisobutyl-aluminium hydride or $NaAl(OCH_2CH_2OCH_3)_2H_2$, and also diborane, if appropriate with addition of catalysts such as $BF_3$, $AlCl_3$ or LiBr. Solvents which are suitable for this purpose are in particular ethers, such as diethyl ether, di-n-butyl ether, THF, dioxane, diglyme or 1,2-dimethoxyethane, and also hydrocarbons, such as benzene. For a reduction with $NaBH_4$, alcohols such as methanol or ethanol, furthermore water and also aqueous alcohols are primarily suitable as solvents. The reduction according to these methods is preferably carried out at temperatures between −80 and +150° C., in particular between 0 and approximately 100° C.

The compounds of the formula I can also be obtained by releasing them from their functional derivatives by solvolysis, in particular by hydrolysis, or by hydrogenolysis.

Preferred starting materials for the solvolysis or hydrogenolysis are those which otherwise correspond to the formula I but, in place of one or more free hydroxyl groups, contain appropriately protected hydroxyl groups, preferably those which, in place of an H atom of a hydroxyl group, carry a hydroxyl protective group.

The term "hydroxyl protective group" is generally known and refers to groups which are suitable for protecting a hydroxyl group from chemical reactions but which can easily be removed after the desired reaction has been carried out elsewhere in the molecule. Typical groups of this type are the abovementioned unsubstituted or substituted aryl, arylalkyl or acyl groups, furthermore also alkyl groups. The nature and the size of the hydroxyl protective groups is again not critical, because they are removed again after the desired chemical reaction or sequence of reactions. However, preference is given to protective groups having 1–20, in particular 1–10, C atoms. Examples of such hydroxyl protective groups are, inter alia, tert-butyl, benzyl, p-nitrobenzoyl, p-toluenesulfonyl and acetyl, with benzyl and acetyl being particularly preferred.

The compounds of the formula I are liberated from their functional derivatives, for example, depending on the protective group used, with strong acids, such as hydrochloric acid or sulfuric acid, strong carboxylic acids, such as trichloroacetic acid, or sulfonic acids, such as benzene- or p-toluene sulfonic acid. This may, if required, be carried out in the presence of an additional solvent.

Inert solvents which are suitable for this purpose are in particular organic solvents, specifically carboxylic acids, such as acetic acid, ethers, such as tetrahydrofuran, amides, such as dimethylformamide, halogenated hydrocarbons, such as dichloromethane, furthermore also alcohols, such as methanol, ethanol or isopropanol, and also water. However, it is also possible to employ mixtures of these solvents. To this end, preference is given to choosing physiologically acceptable inert solvents, or those which, should minute residues remain in the finished product, do not pose any health risk.

Trifluoroacetic acid is preferably used in excess without the addition of another solvent. In contrast, perchloric acid is employed in a mixture of acetic acid and 70% strength perchloric acid in a ratio of 9:1. The protective groups are advantageously cleaved off at temperatures of approximately 0–50° C., preferably at 15–30° C. or room temperature.

Tert-butoxycarbonyl is preferably cleaved off using 40% strength trifluoroacetic acid in dichloromethane or, if it is not possible by other means, using approximately 3 to 5 n HCl in dioxane at 15–60° C. 9-fluorenylmethoxycarbonyl groups are cleaved off using an approximately 5–20% strength solution of dimethylamine, diethylamine or piperidine in DMF at 15–50° C. Elimination of 2,4-dinitrophenyl groups takes place with an approximately 3–10% strength solution of 2-mercaptoethanol in DMF/water at 15–30° C.

Protective groups which can be removed by hydrogenolysis, such as benzyloxymethyl, benzyloxycarbonyl or benzyl, can be cleaved off by treatment with hydrogen in the presence of a catalyst (for example noble metal catalysts such as palladium, advantageously on a support such as carbon). Solvents which are suitable for this purpose are the abovementioned solvents, in particular alcohols, such as methanol or ethanol, or amides, such as DMF. The hydrogenolysis is usually carried out at temperatures between 0 and 100° C. and at pressures between 1 and 200 bar, preferably at 20–30° C. and 1–10 bar. Successful hydrogenolysis of benzyloxycarbonyl groups takes place, for example, on 5–10% strength Pd-C in methanol at 20 to 30° C.

It is furthermore possible where appropriate for a compound of the formula I to be converted by methods known per se into another compound of the formula I.

Thus, appropriate ethers can be cleaved, resulting in the corresponding hydroxyl derivatives. Such ethers may also be cleaved by treatment with a dimethyl sulfide/boron tribromide complex in a solvent, such as toluene, 1,2-dichloroethane, THF or dimethyl sulfoxide, or by melting with pyridine hydrohalides or aniline hydrohalides. This reaction is preferably carried out using pyridine hydrochloride at about 150–250° C., using HBr/acetic acid or using Al trihalides in chlorinated hydrocarbons such as 1,2-dichloroethane.

The compound of the formula I has an asymmetric centre. It can therefore be obtained as a racemate or, if an optically active starting material is employed, also in optically active form. If desired, the racemate which is obtained can be separated physically or chemically by methods known per se. Preference is given to forming diastereomers from racemates by chemical reaction with an optically active resolving agent. Examples of suitable resolving agents are optically active acids, such as the D and L forms of tartaric acid, dibenzoyltartaric acid, diacetyltartaric acid, camphorsulfonic acid, mandelic acid, malic acid or lactic acid. The different forms of the diastereomers can be separated in a manner known per se, for example by fractional crystallization, and the optically active compounds of the formula I can be liberated in a manner known per se from the diastereomers.

A resulting base of the formula I can be converted with an acid into the relevant acid addition salt. Particularly suitable acids for this reaction are those which afford physiologically acceptable salts. Inorganic acids which are suitable for this purpose are sulfuric acid, hydrohalic acids, such as HCl, HBr, phosphoric acids, such as orthophosphoric acid, nitric acid, sulfaminic acid, furthermore organic acids, specifically aliphatic, alicyclic, araliphatic, aromatic or heterocyclic mono- or polybasic carboxylic, sulfonic or sulfuric acids, such as formic acid, acetic acid, propionic acid, pivalic acid, diethylacetic acid, malonic acid, succinic acid, pimelic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid, acid addition salts which are not physiologically acceptable can be used to isolate and purify bases of the formula I.

The free bases of the formula I may, if desired, be liberated from their salts by treatment with strong bases, such as sodium hydroxide or potassium hydroxide, sodium carbonate or potassium carbonate.

The compounds of the general formula I and their physiologically acceptable salts can therefore be used to produce pharmaceutical preparations by converting them together with at least one carrier or auxiliary and, if desired, with one or more other active compounds into the suitable dosage form.

The resulting preparations can be employed as pharmaceuticals in human or veterinary medicine.

Suitable carriers are organic or inorganic substances which are suitable for enteral (for example oral or rectal), parenteral or topical administration and do not react with the novel compounds, for example water, vegetable oils, benzyl alcohols, polyethylene glycols, gelatin, carbohydrates, such as lactose or starch, cellulose, magnesium stearate, talc or petroleum jelly, glycerol triacetate and other fatty acid glycerides, soya lecithin.

Used for oral administration are, in particular, tablets, coated tablets, capsules, syrups, juices or drops. Of specific interest are film-coated tablets and capsules having coatings or capsule shells which are resistant to gastric juices. Used for rectal administration are suppositories, used for parenteral administration are solutions, preferably oily or aqueous solutions, furthermore suspensions, emulsions or implants, and used for topical administration are ointments, creams or powders.

It is also possible to lyophilize the active compounds claimed according to the invention and to use the resulting lyophilizates, for example, for producing preparations for injection.

The stated preparations can be sterilized and/or contain auxiliaries, such as lubricants, preservatives, stabilizers and/or wetting agents, emulsifiers, salts to influence the osmotic pressure, buffer substances, colorants and/or flavourings. They may be also, if desired, contain one or more other active compounds, for example one or more vitamins, diuretics, antiphlogistics.

The compound of the formula I and physiologically acceptable salts thereof can be employed for the therapeutic treatment of the human or animal body, in particular for controlling diseases. It is effective in the treatment of schizophrenia and of affective disorders, such as, for example, depression and/or anxiety. The compound can also be used in the treatment of extrapyrimidal disorders. The compound according to the invention is effective as a neuroleptic, but has, in an advantageous manner, no significant cataleptic side effects. The compound is furthermore effective in the treatment of stroke.

The compound according to formula I according to the invention and physiologically acceptable salts thereof are usually administered in analogy to other known products obtainable commercially for the claimed indications (thioridazine, haloperidol), preferably in dosages between approximately 0.1 mg and 500 mg, in particular between 0.2 and 50 mg, per dosage unit. The daily dosage is preferably between approximately 0.002 and 20 mg/kg, in particular between 0.2 and 0.4 mg/kg of body weight.

The specific dose for each patient depends, however, on a wide variety of factors, for example on the activity of the specific compound employed, on the age, body weight, general state of health, sex, on the diet, on the time and route of administration, on the rate of excretion, combination of medicinal substances and severity of the particular disorder for which the therapy applies. Oral administration is preferred. Hereinbelow, examples are given which serve to illustrate the invention, but the invention is not limited to the examples given.

Owing to its molecular structure, the compound of the formula I according to the invention can occur in two enantiomeric forms. It can therefore be present in racemic or in optically active form.

Since the pharmaceutical activity of the racemates or the stereoisomers of the compound according to the invention may differ, it may be desirable to employ the enantiomers. In these cases, the end product or else even the intermediates may be separated into enantiomeric compounds by chemical or physical means known to the person skilled in the art, or may even be employed as such in the synthesis.

In the case of racemic amines, diastereomers are formed from the mixture by reaction with an optically active resolving agent. Examples of suitable resolving agents are optically active acids such as the R and S forms of tartaric acid, diacetyltartaric acid, dibenzoyltartaric acid, mandelic acid, malic acid, lactic acid, suitable N-protected amino acids (for example N-benzoylproline or N-benzenesulfonylproline) or the various optically active camphorsulfonic acids. It is also advantageous to separate the entantiomers by chromatography using an optically active resolving agent (for example dinitrobenzoylphenylglycine, celluose triacetate or other derivatives of carbohydrates or chirally derivatized methacrylate polymers immobilized on silica gel). Suitable mobile phases for this purpose are aqueous or alcoholic solvent mixtures, such as, for example, hexane/isopropanol/acetonitrile, for example in the ratio 82:15:3.

Salts with physiologically unacceptable acids, for example picrates, can be used to isolate and/or purify the compounds of the formula I.

In the examples below, "usual" work-up means: if necessary, water is added, extraction is carried out with dichloromethane, the mixture is separated, the organic phase is dried over sodium sulfate, filtered, evaporated and purified by silica gel chromatography and/or by crystallization. All temperatures are given in ° C., and the $[\alpha]_D$ values are measured at 20° C. in dimethyl sulfoxide.

EXAMPLE 1

A solution comprising 4.92 g of (5R)-(−)-5-(methanesulfonyloxymethyl)-3-p-hydroxyphenyl-oxazolidin-2-one [obtainable from (5R) -(−) -5-(methane-sulfonyloxymethyl)-3-p-methoxyphenyloxazolidin-2-one by treatment with boron tribromide in dichloromethane], 65 ml of acetonitrile, 4.70 g of 4-(4-fluorobenzyl)-piperidine hydrochloride and 4.43 g of sodium bicarbonate is stirred under reflux conditions for a period of 26 hours. The reaction mixture is subsequently diluted with 100 ml of dichloromethane, extracted repeatedly with a small amount of water and dried. After drying, the solvent is distilled off and the resulting product is purified chromatographically over a silica gel column. In this manner, the reaction product is obtained as colourless resin, which is crystallized out.
Yield: (5S)-(−)-5-[4-(4-fluorobenzyl)-1-piperidinyl-methyl]-3-(4-hydroxyphenyl) oxazolidin-2-one
m.p. 164–165°
$[\alpha]_D^{20}=-28.0°$ By reaction with methanesulfonic acid in acetone, 3.18 g of (5S)-(−)-5-[4-(4-fluorobenzyl)-1-piperidinylmethyl]-3-(4-hydroxyphenyl)oxazolidin-2-one, methane sulfonate, are obtained
m.p. 234–236°
$[\alpha]_D^{20}=-33.3°$.

EXAMPLE 2

At atmospheric pressure and 20° C., a solution of 1 g of (5S)-(−)-5-[4-(4-fluorobenzyl)-1-piperidinyl-methyl]-3-(4-benzyloxyphenyl)oxazolidin-2-one [obtainable by reaction of (5R)-(−)-5-(methanesulfonyloxy-methyl) -3-p-benzyloxyphenyloxazolidin-2-one with 4- (4-fluorobenzyl) piperidine hydrochloride] in 25 ml of methanol is hydrogenated over 1 g of Raney nickel. The mixture is filtered and the solvent is removed, giving (5S)-(−)-5-[4-(4-fluorobenzyl)-1-piperidinylmethyl]-3-(4-hydroxyphenyl) oxazolidin-2-one,
m.p. 164–165°
$[\alpha]_D^{20}=-28.0°$

EXAMPLE 3

A solution of 1 g of (5S)-(−)-5-[4-(4-fluorobenzyl)-1-piperidinylmethyl]-3-(4-methoxyphenyl)-oxazolidin-2-one [obtainable by reaction of (5R)-(−)-5-(methanesulfonyloxymethyl)-3-p-methoxyphenyloxazolidin-2-one with 4- (4-fluorobenzyl) piperidine hydrochloride] in 25ml of dichloromethane is mixed with equimolar amounts of boron tribromide and stirred for 1 hour. Usual work-up gives (5S)-(−)-5-[4-(4-fluorobenzyl)-1-piperidinylmethyl]-3-(4-hydroxyphenyl)-oxazolidin-2-one,
m.p. 164–165°
$[\alpha]_D^{20}=-28.0°$.

Pharmacological tests

1. Ifenprodil binding (Schoemaker et al., 1990)

Homogenates of rat forebrain were centrifuged repeatedly. The last membrane supernatant (10 mg/ml) was used to determine the specific binding in the presence of 1.15 nM [$^3$H]-ifenprodil in 5 ml of buffer solution at pH 7.4. The unspecific binding was determined in the presence of 100 $\mu$M of ifenprodil.

2. Inhibition of apomorphine-induced stereotypical behaviour in rats (Puech et al., 1978):

Stereotypical behaviour (unmotivated sniffling, licking, chewing, rhythmic movements with the forepaws) was induced by administration of 0.5 mg/kg s.c. of apomorphine. The intensity of the ensuing stereotypical behaviour was assessed every 5 minutes for each rat for a period of 30 minutes using a rating system (0–3). The total score was used as a measure of the occurence of the stereotypical behaviour.

3. Catalepsy induction in rats (Stanley and Glick, 1976):

The occurrence of catalepsy in rats was measured by placing a hindpaw on a 3 cm high block and scoring every 5 minutes for a period of 30 minutes the time for which the rat stayed in this unnatural position using a rating system (score 0–3). The total score was used as a measure of the intensity of the catalepsy.

The test results with the 5S enantiomer of the compound according to the invention and the comparative compounds A, B and C are summarized in Table I below.

TABLE I

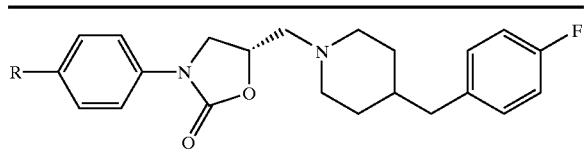

| | R = OH | R = CH₃ | R = F | R = OCH₃ |
|---|---|---|---|---|
| Ifenprodil binding in vitro 50% displacement/IC$_{50}$ | 0.01 $\mu$M | >1 $\mu$M | >1 $\mu$M | >1 $\mu$M |

TABLE I-continued

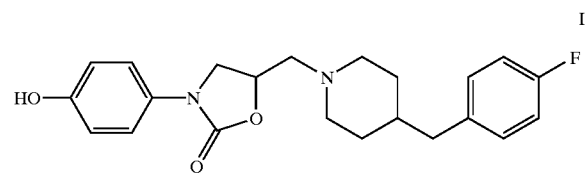

|  | R = OH | R = CH₃ | R = F | R = OCH₃ |
|---|---|---|---|---|
| at: Inhibition of apomorphine-induced stereotypical behaviour in rats 50% inhibition/$ED_{50}$ s.c. at: | 2.8 mg/kg | >10 mg/kg | >10 mg/kg | >10 mg/kg |
| Catalepsy induction Rat | 30 mg/kg s.c. 0% | not tested | not tested | not tested |

The tested compounds were employed in the form of their methanesulfonate salts.

In vitro, the compound (5S)-(−)-5-[4-(4-fluorobenzyl)-1-piperidinylmethyl]-3-(4-hydroxyphenyl)-oxazolidin-2-one is a potent ligand in the nanomolar concentration range (IC50=10 nM) for the polyamine binding site, which represents a modulating binding site for the N-methyl-D-aspartate subtype of the glutamate binding sites.

The compound inhibits apomorphine-induced stereotypical behaviour in rats ($ED_{50}$ 2.8 mg/kg s.c.), which is seen as proof for neuroleptic action.
It is assumed that the compound does not cause any extrapyrimidal side effects, since it does not cause catalepsy in vivo in appropriate animal models ($ED_{50}$>>30 mg/kg).
The compound represents a new active principle for the treatment of schizophrenia.

The following examples relate to pharmaceutical preparations:

Example A: Vials
A solution of 100 g of an active compound of the formula I and 5 g of disodium hydrogen phosphate in 3 l of double-distilled water is adjusted to pH 6.5 with 2 n hydrochloric acid, sterilized by filtration, dispensed into vials, lyophilized under sterile conditions and closed sterile. Each vial contains 5 mg of active compound.

Example B: Suppositories
A mixture of 20 mg of an active compound of the formula I is melted with 100 g of soya lecithin and 1400 g of cocoa butter, poured into moulds and left to cool. Each suppository contains 20 mg of active compound.

Example C: Solution
A solution of 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water is prepared. The solution is adjusted to pH 6.8, made up to 1 l and sterilized by irradiation.

Example D: Ointment
500 mg of an active compound of the formula I are mixed with 99.5 g of petrolatum under aseptic conditions.

Example E: Tablets
A mixture of 1 kg of active compound of the formula I, 4 kg of lactose, 1.2 kg of potato starch, 0.2 kg of talc and 0.1 kg of magnesium stearate is compressed to tablets in a conventional way so that each tablet contains 10 mg of active compound.

Example F: Coated tablets
Tablets are compressed in analogy to Example E and are subsequently coated in a conventional way with a coating of sucrose, potato starch, talc, tragacanth and colorant.

Example G: Capsules
2 kg of active compound of the formula I are packed in hard gelatin capsules in a conventional way so that each capsule contains 20 mg of the active compound.

Example H: Ampoules
A solution of 1 kg of active compound of the formula I in 60 l of double-distilled water is sterilized by filtration, dispensed into ampoules, lyophilized under sterile conditions and closed sterile.
Each ampoule contains 10 mg of active compound.

What is claimed is:
1. The compound 5-[4-(4-fluorobenzyl)piperidin-1-ylmethyl]-3-(4-hydroxyphenyl) oxazoldin-2-one of formula I

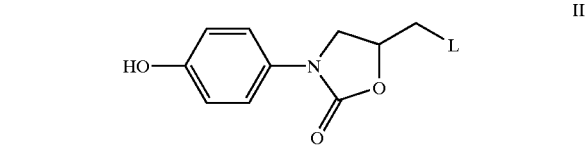

or a physiologically acceptable salt thereof.
2. A compound according to claim 1, wherein said compound is in the form of a separate enantiomer.
3. A process for preparing a compound according to claim 1, comprising
   a) reacting a compound of formula II

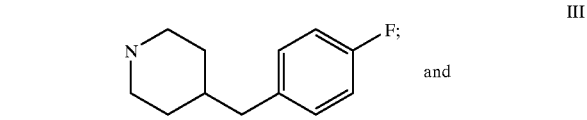

wherein
   L is Cl, Br, I or a free or reactively functionally modified OH group, with a compound of formula III optionally converting a basic compound of the formula I into one of its salts by treatment with an acid.
4. A pharmaceutical composition comprising an effective amount of a compound according to claim 1, and a pharmaceutically acceptable carrier.
5. A method for inducing a neuroleptic effect in a patient comprising administering to said patient a neuroleptic effective amount of a compound according to claim 1.
6. A method according to claim 5, wherein said compound is administered in a daily amount of 0.002–20 mg/kg of bodyweight.
7. A method according to claim 6, wherein said compound is administered in a daily amount of 0.2–0.4 mg/kg of bodyweight.
8. A composition according to claim 4, wherein said composition contains 0.1–500 mg of said compound.
9. A compound according to claim 1, wherein said compound is
   (5S)-(−)-5-[4-(4-fluorobenzyl)-1-piperidinylmethyl]-3-(4-hydroxyphenyl)-oxazolidin-2-one, or a pharmaceutically acceptable salt thereof.

10. A compound according to claim 9, wherein said compound is (5S)-(−)-5-[4-(4-fluorobenzyl)-1-piperidinylmethyl]-3-(4-hydroxyphenyl)-oxazolidin-2-one.

11. A process according to claim 3, wherein the reaction between the compound of formula II and the compound of formula III is carried out in an inert solvent in the presence of an acid binder.

12. A method according to claim 11, wherein said reaction is also carried out in the presence of an organic base.

13. A process according to claim 3, wherein the reaction is performed at a temperature of 0–150° C.

14. A process according to claim 13, wherein said reaction is performed at a temperature of 20–30° C.

15. A compound according to claim 1, wherein said compound is in an optically active form.

16. A compound according to claim 1, wherein said compound is in the form of a racemate.

17. A process according to claim 3, wherein the reaction between the compounds of formula II and the compound of formula III yields a racemate, and said process further comprises forming diastereomers of said racemate by reaction with an optically reactive resolving agent, and then separating said diastereomers.

18. A method according to claim 3, wherein a base of formula I is converted with an acid into a relevant acid addition salt, and said acid is HCl, HBr, orthophosphoric acid, nitric acid sulfaminic acid, formic acid, acetic acid, propionic acid, pivalic acid, diethylacetic acid, malonic acid, succinic acid, pimelic acid, citric acid, gluconic acid, ascorbic acid, nicotinic acid, isonicotrinic acid, methanesulfonic acid, ethanesulfonic acid, ethanedisulfonic acid, 2-hydroxyethanesulfonic acid, benzenesulfonic acid, p-toluenesulfonic acid, naphthalenemono sulfonic acid, naphthalene disulfonic acid, or laurylsulfuric acid.

19. A method according to claim 5, wherein said patient is suffering from schizophrenia.

20. A method according to claim 3, wherein L is Cl, Br, I, OH or sylfonyloxy derivative of an OH group.

21. A method according to claim 19, wherein said compound is administered in a daily amount of 0.002–20 mg/kg of body weight.

22. A method according to claim 21, wherein said compound is administered in a daily amount of 0.2–0.4 mg/kg of body weight.

* * * * *